United States Patent
Takei

(10) Patent No.: US 8,315,448 B2
(45) Date of Patent: Nov. 20, 2012

(54) MEDICAL IMAGE PROCESSING APPARATUS AND MEDICAL IMAGE PICKUP SYSTEM

(75) Inventor: Shunji Takei, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 90 days.

(21) Appl. No.: 12/832,398

(22) Filed: Jul. 8, 2010

(65) Prior Publication Data

US 2010/0278404 A1   Nov. 4, 2010

Related U.S. Application Data

(63) Continuation of application No. PCT/JP2008/068788, filed on Oct. 16, 2008.

(30) Foreign Application Priority Data

Jan. 11, 2008 (JP) .................... 2008-004789

(51) Int. Cl.
*G06K 9/00* (2006.01)
(52) U.S. Cl. ....................... 382/128; 382/131
(58) Field of Classification Search .............. 382/128; 348/71, 65, 70, 77
See application file for complete search history.

(56) References Cited

U.S. PATENT DOCUMENTS

| | | | |
|---|---|---|---|
| 4,658,284 A * | 4/1987 | Kawamura et al. | 348/458 |
| RE34,504 E * | 1/1994 | Uehara et al. | 348/65 |
| 5,667,474 A * | 9/1997 | Nishimura | 600/109 |
| 6,614,472 B1 * | 9/2003 | Yamashita | 348/243 |
| 6,900,829 B1 * | 5/2005 | Ozawa et al. | 348/71 |
| 7,304,669 B2 * | 12/2007 | Aizawa et al. | 348/231.7 |
| 7,859,492 B2 * | 12/2010 | Kohno | 345/77 |
| 2003/0118106 A1 * | 6/2003 | Kondo et al. | 375/240.16 |
| 2006/0058684 A1 * | 3/2006 | Sendai | 600/476 |
| 2007/0153542 A1 * | 7/2007 | Gono et al. | 362/574 |
| 2009/0021578 A1 * | 1/2009 | Yamazaki et al. | 348/65 |
| 2009/0036741 A1 * | 2/2009 | Igarashi et al. | 600/160 |
| 2009/0066787 A1 * | 3/2009 | Yamazaki | 348/70 |
| 2011/0152614 A1 * | 6/2011 | Takei | 600/109 |
| 2011/0237894 A1 * | 9/2011 | Ozawa et al. | 600/168 |
| 2012/0078046 A1 * | 3/2012 | Sasaki et al. | 600/109 |

FOREIGN PATENT DOCUMENTS

| | | |
|---|---|---|
| JP | 05-084218 | 4/1993 |
| JP | 05-111459 | 5/1993 |
| JP | 05-207973 | 8/1993 |
| JP | 05-237059 | 9/1993 |
| JP | 06-225854 | 8/1994 |

(Continued)

*Primary Examiner* — Chan S Park
*Assistant Examiner* — Nancy Bitar
(74) *Attorney, Agent, or Firm* — Scully, Scott, Murphy & Presser, P.C.

(57) ABSTRACT

A medical image processing apparatus of the present invention is a medical image processing apparatus to which a plurality of color components corresponding to frame-sequentially picked-up images of an object are time-sequentially inputted while maintaining periodicity thereof, including a color component storage section that can store a first color component inputted to the medical image processing apparatus at one timing and a second color component, which is a component of the same wavelength band as that of the first color component inputted to the medical image processing apparatus at timing preceding the one timing by one cycle or more, and an image correction processing section that simultaneously reads the first color component and the second color component stored in the color component storage section and performs image correction processing.

9 Claims, 6 Drawing Sheets

FOREIGN PATENT DOCUMENTS

| | | |
|---|---|---|
| JP | 06-296581 | 10/1994 |
| JP | 08-338953 | 12/1996 |
| JP | 09-073034 | 3/1997 |
| JP | 09-102958 | 4/1997 |
| JP | 09-130666 | 5/1997 |
| JP | 09-138356 | 5/1997 |

* cited by examiner

MEDICAL IMAGE PROCESSING APPARATUS AND MEDICAL IMAGE PICKUP SYSTEM

CROSS REFERENCE TO RELATED APPLICATION

This application is a continuation application of PCT/JP2008/068788 filed on Oct. 16, 2008 and claims benefit of Japanese Application No. 2008-004789 filed in Japan on Jan. 11, 2008, the entire contents of which are incorporated herein by this reference.

BACKGROUND OF INVENTION

1. Field of the Invention

The present invention relates to a medical image processing apparatus and a medical image pickup system, and more particularly, to a medical image processing apparatus and a medical image pickup system capable of frame-sequentially acquiring color components of an object.

2. Description of the Related Art

Medical systems made up of an endoscope and a medical image processing apparatus or the like are conventionally mainly used by an operator or the like to observe the inside of a living body as an object to be examined. Examples of the endoscope system used for the above described application include an electronic endoscope apparatus proposed in Japanese Patent Application Laid-Open Publication No. 5-237059.

The electronic endoscope apparatus described in Japanese Patent Application Laid-Open Publication No. 5-237059 has a configuration based on a so-called frame sequential image pickup method (hereinafter referred to as "frame sequential method"), and to be more specific, is configured by including illumination means for time-sequentially illuminating an object with a plurality of illumination lights of different wavelength bands, a solid image pickup device that picks up an image of the object illuminated with the illumination lights from the illumination means and reading means for dividing information of the solid image pickup device into information of odd-numbered fields and information of even-numbered fields through interlace scanning and alternately reading the information.

SUMMARY OF THE INVENTION

A medical image processing apparatus according to the present invention is a medical image processing apparatus to which a plurality of color components corresponding to frame-sequentially picked-up images of an object are time-sequentially inputted while maintaining periodicity thereof, including a color component storage section that can store a first color component inputted to the medical image processing apparatus at one timing and a second color component, which is a component of the same wavelength band as that of the first color component inputted to the medical image processing apparatus at timing preceding the one timing by one cycle or more, and an image correction processing section that simultaneously reads the first color component and the second color component stored in the color component storage section and performs image correction processing.

A medical image pickup system according to the present invention includes a light source section that time-sequentially outputs a plurality of illumination lights of different wavelength bands, a color component acquiring section that can receive returned light from an object illuminated with the illumination lights and acquires color components of the object corresponding to the returned light, a color component storage section that can store a first color component acquired at one timing corresponding to a cycle in which light of the same wavelength band is outputted from the light source section and a second color component, which is a component of the same wavelength band as that of the first color component acquired at timing preceding the one timing by one cycle or more and an image correction processing section that simultaneously reads the first color component and the second color component stored in the color component storage section and performs image correction processing.

DETAILED DESCRIPTION OF THE PREFERRED EMBODIMENT(S)

Hereinafter, an embodiment of the present invention will be described with reference to the accompanying drawings.

Figure 1:
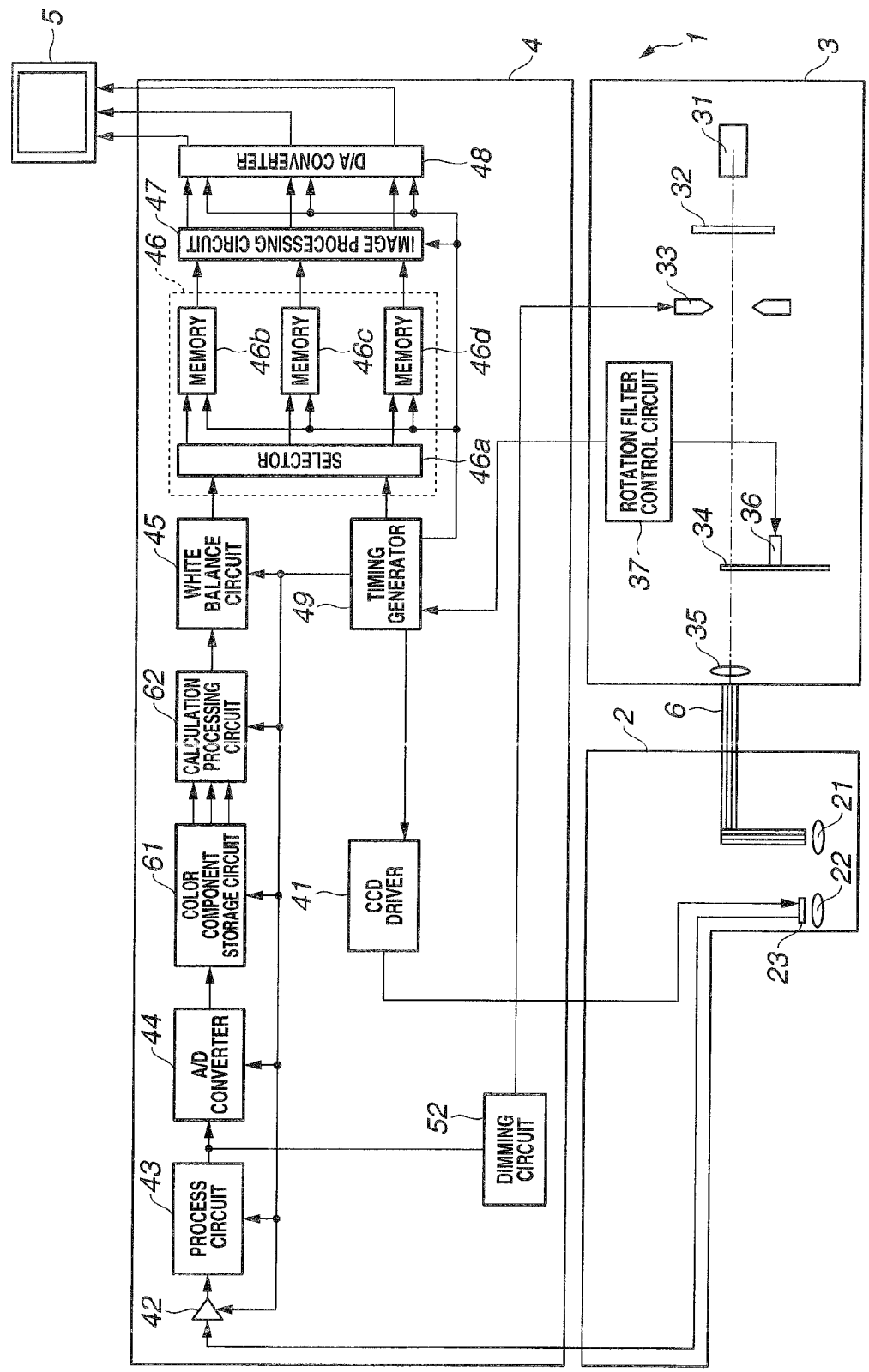
FIG. 1 is a diagram illustrating an example of a configuration of main parts of an endoscope apparatus as a medical image pickup system for which a medical image processing apparatus according to the present embodiment is used.
Figure 2:
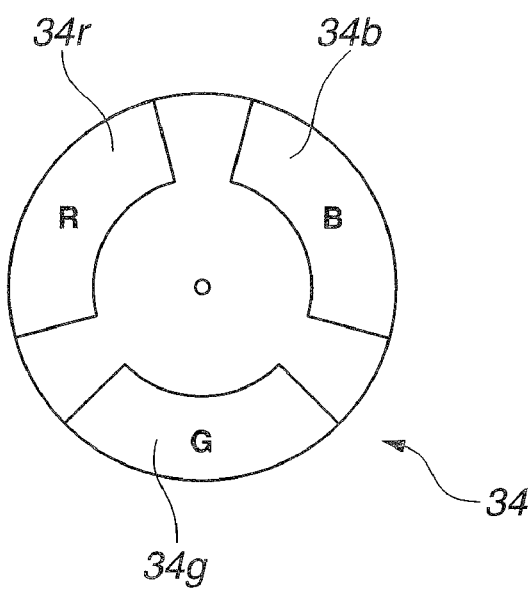
FIG. 2 is a diagram illustrating an example of a configuration of a rotation filter of the endoscope apparatus in FIG. 1.
Figure 3:
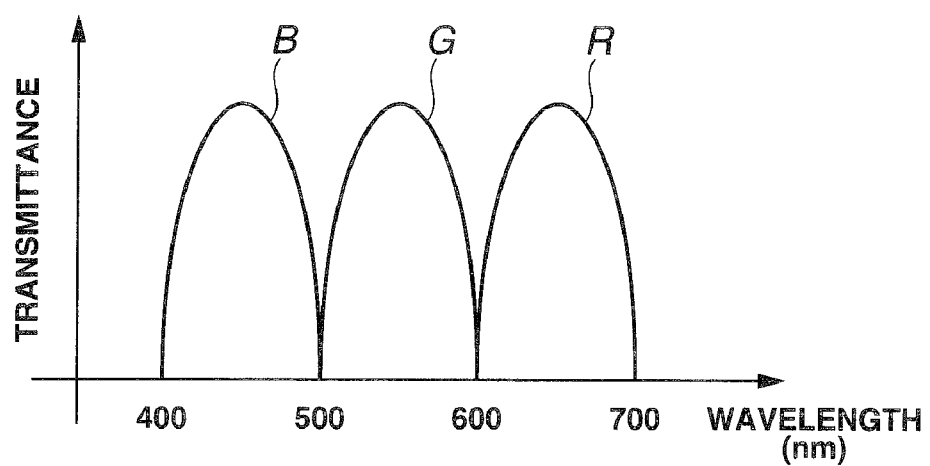
FIG. 3 is a diagram illustrating an example of transmission characteristics of each filter of the rotation filter in FIG. 2.
Figure 4:
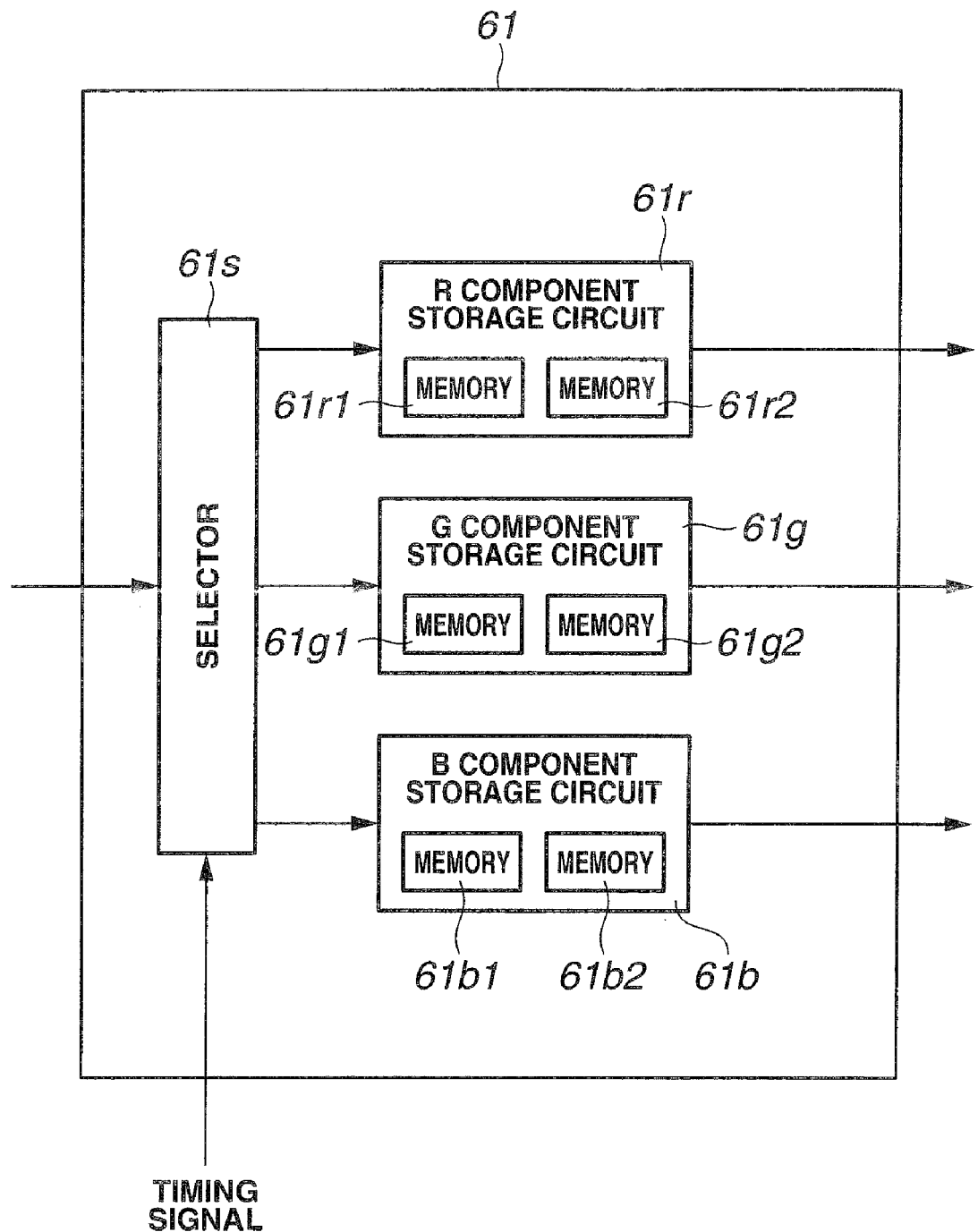
FIG. 4 is a diagram illustrating an example of a configuration of the color component storage circuit according to the present embodiment.
Figure 5:
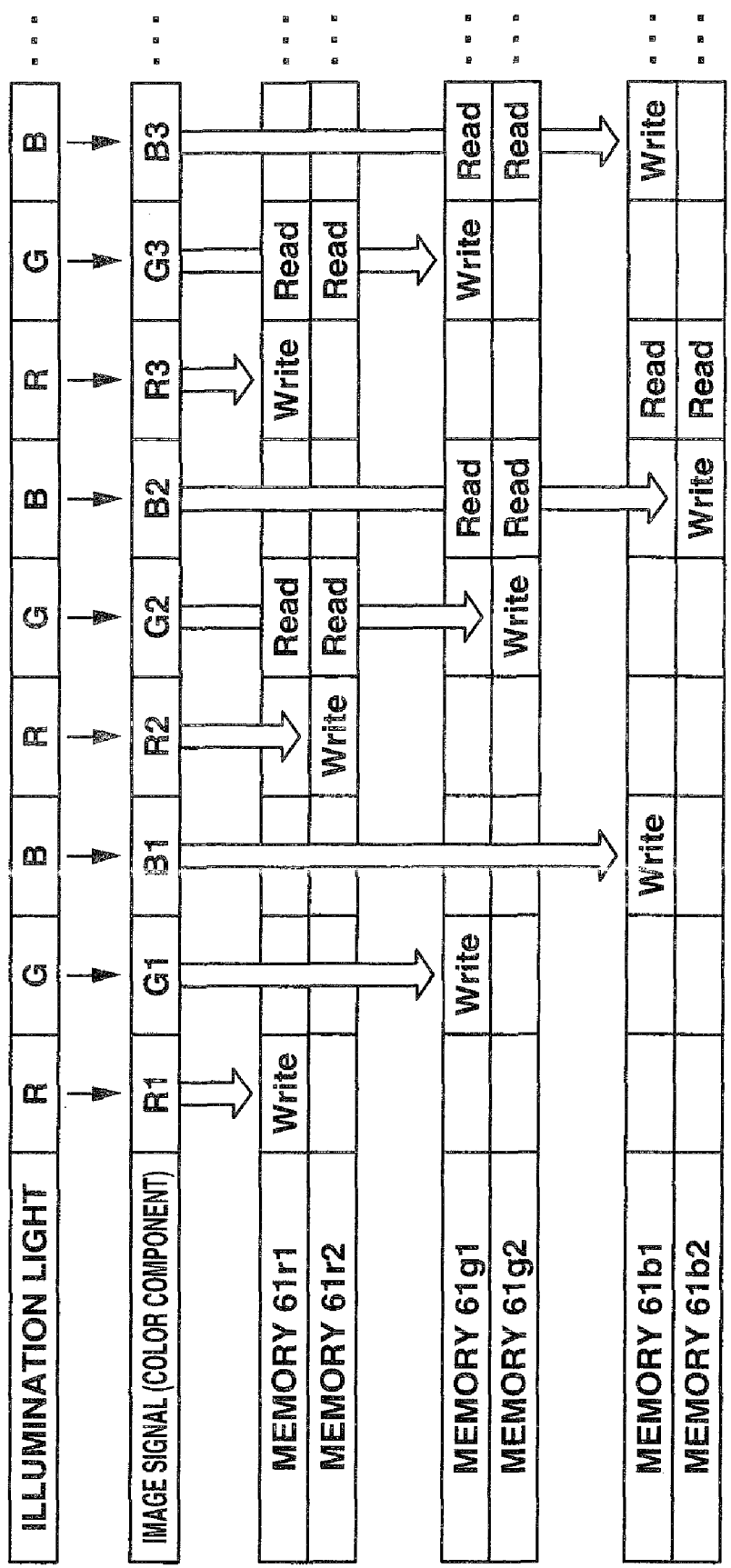
FIG. 5 is a diagram illustrating write timing and read timing of each color component in the color component storage circuit in FIG. 4.
Figure 6:
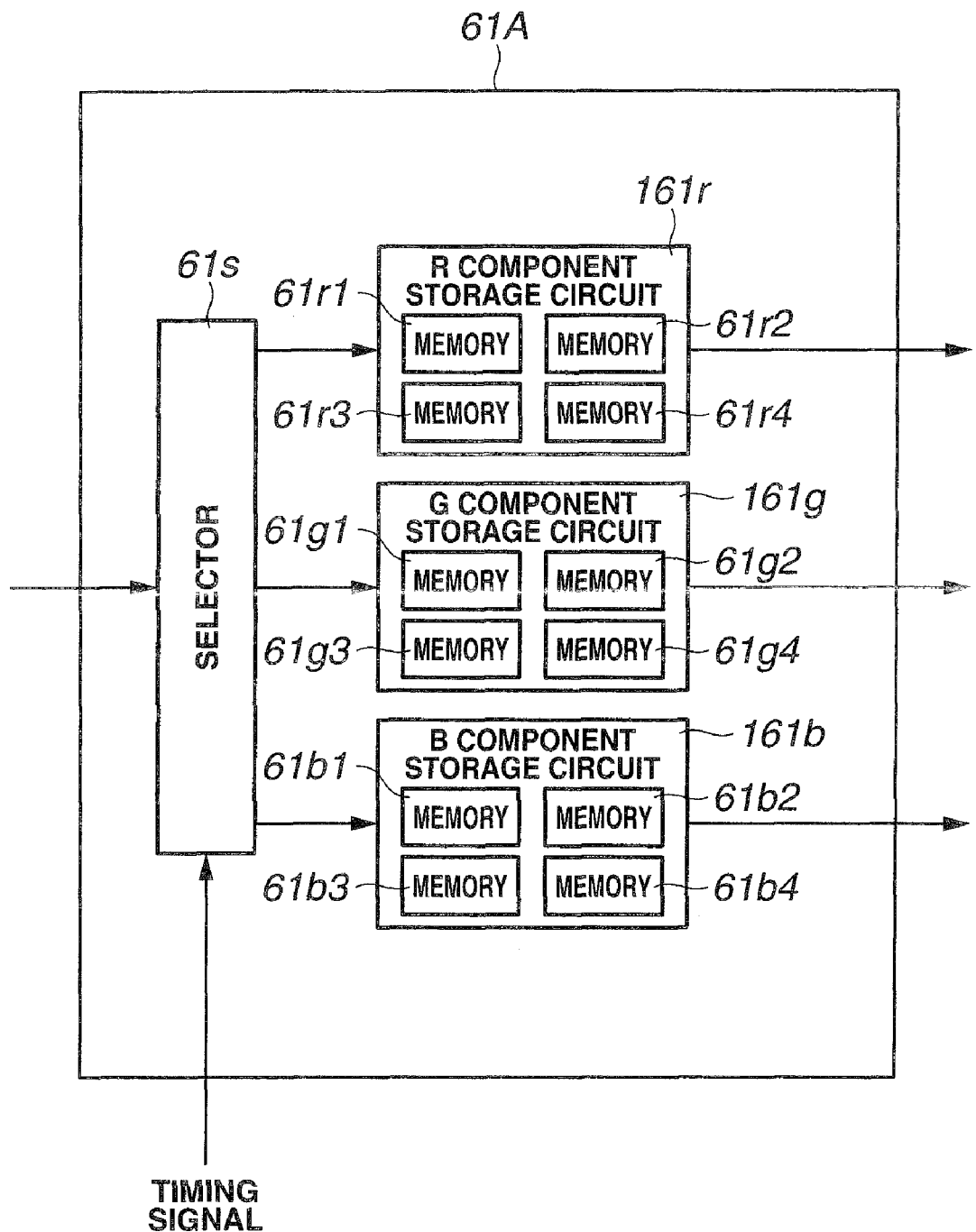
FIG. 6 is a diagram illustrating an example different from that in FIG. 4 of the configuration of the color component storage circuit according to the present embodiment.
Figure 7:
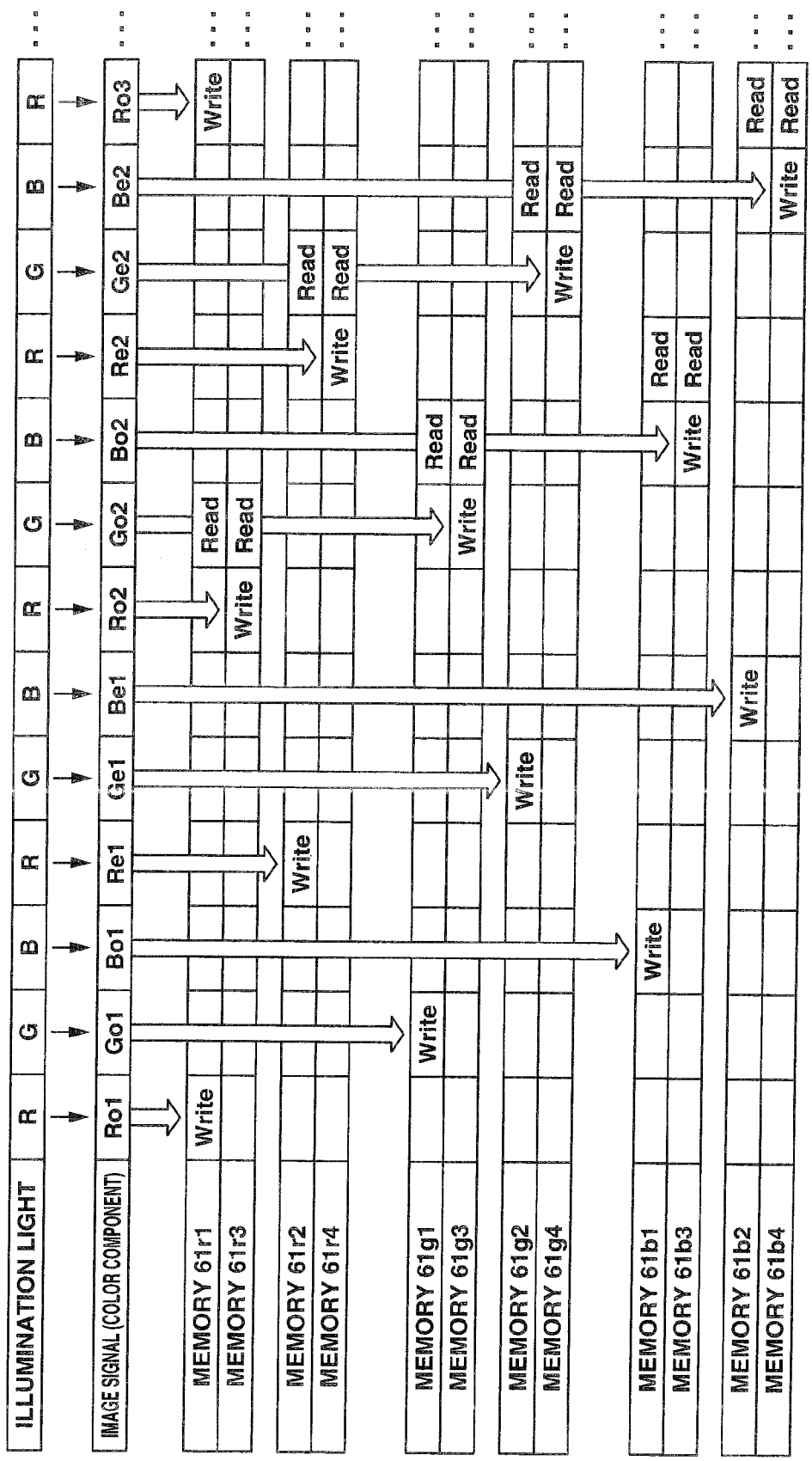
FIG. 7 is a diagram illustrating write timing and read timing of each color component in the color component storage circuit in FIG. 6.

FIGS. 1 to 7 are related to the embodiment of the present invention. FIG. 1 is a diagram illustrating an example of a configuration of main parts of an endoscope apparatus as a medical image pickup system for which a medical image processing apparatus according to the present embodiment is used. FIG. 2 is a diagram illustrating an example of a configuration of a rotation filter of the endoscope apparatus in FIG. 1. FIG. 3 is a diagram illustrating an example of transmission characteristics of each filter of the rotation filter in FIG. 2. FIG. 4 is a diagram illustrating an example of a configuration of the color component storage circuit according to the present embodiment. FIG. 5 is a diagram illustrating write timing and read timing of each color component in the color component storage circuit in FIG. 4. FIG. 6 is a diagram illustrating an example different from that in FIG. 4 of the configuration of the color component storage circuit according to the present embodiment. FIG. 7 is a diagram illustrating write timing and read timing of each color component in the color component storage circuit in FIG. 6.

As shown in FIG. 1, an endoscope apparatus 1 as a medical image pickup system of the present embodiment is configured by including, as main components, an endoscope 2 that can be inserted into a living body, picks up an image of an object such as living tissue existing in the living body and outputs the image of the living tissue as an image pickup signal, a light source apparatus 3 that supplies illumination light for illuminating the object to the endoscope 2 via a light guide 6 inserted in the endoscope 2, a video processor 4 that performs signal processing according to the image pickup signal outputted from the endoscope 2 and outputs the image pickup signal after the signal processing as a video signal and a monitor 5 that displays the image of the object picked up by the endoscope 2 based on the video signal outputted from the video processor 4.

The endoscope 2 is configured by including an illumination optical system 21 that outputs illumination light supplied from the light source apparatus 3 and transmitted by the light guide 6, an objective optical system 22 that forms an image of the object illuminated with illumination light outputted from the illumination optical system 21 and a CCD (charge coupled device) 23 placed at an image forming position of the objective optical system 22.

The progressive scanning (non-interlace scanning) CCD 23 picks up an image of the object illuminated with illumination light time-sequentially outputted from the illumination optical system 21 and outputs the image of the object as an image pickup signal. Thus, the CCD 23 as the image pickup device outputs information of odd-numbered fields and information of even-numbered fields of one color component acquired for one exposure period as an image pickup signal during a read period after the exposure period.

That is, the CCD 23 has a function as a color component acquiring section that can receive returned light from the object illuminated with illumination light time-sequentially outputted from the illumination optical system 21 and acquires color components of the object according to the returned light.

The light source apparatus 3 as a light source section has a lamp 31, a heat radiation cut filter 32 that cuts heat radiation of white color light emitted from the lamp 31, a diaphragm apparatus 33, a rotation filter 34 that transforms the white color light that has passed through the diaphragm apparatus 33 into frame sequential illumination light, a condensing optical system 35 that condenses the frame sequential illumination light that has passed through the rotation filter 34 and outputs the illumination light to the light guide 6, a rotation filter motor 36 that drives the rotation filter 34 to rotate and a rotation filter control circuit 37.

The lamp 31 is a light source that can emit white color light and is made up of, for example, a xenon lamp.

The diaphragm apparatus 33 adjusts the light amount of the white color light that has passed through the heat radiation cut filter 32 based on a diaphragm control signal outputted from the video processor 4.

As shown in FIG. 2, the rotation filter 34 is configured into a disk shape, the center of which is the axis of rotation. Furthermore, as shown in FIG. 2, the rotation filter 34 is configured by including an R filter 34r that allows light in a red color wavelength band to transmit therethrough, a G filter 34g that allows light in a green color wavelength band to transmit therethrough and a B filter 34b that allows light in a blue color wavelength band to transmit therethrough, each filter being provided in a circumferential direction of the perimeter.

The R filter 34r is configured so as to allow light in the red color wavelength band, for example, light from 600 nm to 700 nm as shown in FIG. 3 to transmit therethrough.

The G filter 34g is configured so as to allow light in the green color wavelength band, for example, light from 500 mm to 600 mm as shown in FIG. 3 to transmit therethrough.

The B filter 34b is configured so as to allow light in the blue color wavelength band, for example, light from 400 nm to 500 nm as shown in FIG. 3 to transmit therethrough.

The rotation filter control circuit 37 controls the rotation driving of the rotation filter motor 36 and outputs a synchronization signal synchronized with the rotation of the rotation filter 34 to the video processor 4. With the respective sections of the light source apparatus 3 having the aforementioned configurations, the white color light that has transmitted through the R filter 34r, the G filter 34g and the B filter 34b is condensed by the condensing optical system 35 as frame sequential illumination light made up of R (red) light, G (green) light and B (blue) light and then outputted to the light guide 6.

The video processor 4 is provided with a CCD driver 41 that drives the CCD 23 of the endoscope 2, an amplifier 42 that amplifies an image pickup signal outputted from the CCD 23, a process circuit 43 that applies processing such as correlation double sampling to the image pickup signal outputted from the amplifier 42 and an A/D converter 44 that converts the image pickup signal outputted from the process circuit 43 to a digital image signal.

Furthermore, the video processor 4 is provided with a color component storage circuit 61 that stores the image signal outputted from the A/D converter 44 for each color component and a calculation processing circuit 62.

As shown in FIG. 4, the color component storage circuit 61 as a color component storage section is configured by including a selector 61s that selectively outputs color components included in the image signal from the A/D converter 44 based on a timing signal outputted from a timing generator 49, an R component storage circuit 61r that stores an R component included in the image signal from the selector 61s, a G component storage circuit 61g that stores a G component included in the image signal from the selector 61s and a B component storage circuit 61b that stores a B component included in the image signal from the selector 61s.

The R component storage circuit 61r has memories 61r1 and 61r2 to store two R components; a first R component inputted at predetermined timing and a second R component inputted at timing preceding the predetermined timing by one cycle.

The G component storage circuit 61g has memories 61g1 and 61g2 to store two G components; a first G component inputted at predetermined timing and a second G component inputted at timing preceding the predetermined timing by one cycle.

The B component storage circuit 61b has memories 61b1 and 61b2 to store two B components; a first B component inputted at predetermined timing and a second B component inputted at timing preceding the predetermined timing by one cycle.

The calculation processing circuit 62 sequentially reads at different timing the two R components (first R component and second R component) stored in the R component storage circuit 61r, the two G components (first G component and second G component) stored in the G component storage circuit 61g and the two B components (first B component and second B component) stored in the B component storage circuit 61b sequentially at different timings based on timing signals outputted from the timing generator 49, applies image correction processing such as noise reduction processing and/or motion interpolation processing or the like to information on the read color components and then outputs the color component signals after the image correction processing to a white balance circuit 45.

Furthermore, the video processor 4 is provided with the white balance circuit 45 that applies white balance processing to the color component signals outputted from the calculation processing circuit 62, a synchronization circuit 46 that temporarily stores and synchronizes the color component signals sequentially outputted from the white balance circuit 45, an image processing circuit 47, a D/A converter 48, the timing generator 49 that outputs timing signals corresponding to synchronization signals outputted from the rotation filter control circuit 37 of the light source apparatus 3 to the respective sections of the aforementioned video processor 4 and a dimming circuit 52.

The synchronization circuit 46 is configured by including a selector 46a, and memories 46b, 46c and 46d.

The selector 46a sequentially outputs the color component signals outputted from the white balance circuit 45 to the memories 46b, 46c and 46d based on the timing signals outputted from the timing generator 49.

The memories 46b, 46c and 46d are configured as an R channel memory, a G channel memory and a B channel memory respectively. That is, the color component signal inputted to the memory 46b is stored as a red component, the color component signal inputted to the memory 46c is stored as a green component and the color component signal inputted to the memory 46d is stored as a blue component.

The memories 46b, 46c and 46d store and synchronize the color component signals outputted from the selector 46a based on the timing signals outputted from the timing generator 49.

The image processing circuit 47 reads color component signals corresponding to one frame out of the respective color component signals stored in the synchronization circuit 46, performs processing such as gamma correction processing on the color component signals corresponding to one frame and then outputs the processed color component signals corresponding to one frame to the D/A converter 48.

The D/A converter 48 converts the respective color component signals outputted from the image processing circuit 47 to analog video signals and outputs the analog video signals.

The dimming circuit 52 outputs a diaphragm control signal for performing brightness control according to an observation of white color light based on the image pickup signal outputted from the process circuit 43 to the diaphragm apparatus 33.

Next, operations of the endoscope apparatus 1 will be described.

First, the operator et al. turns on power to the respective sections of the endoscope apparatus 1, that is, the endoscope 2, the light source apparatus 3, the video processor 4 and the monitor 5 to activate the respective sections.

When the light source apparatus 3 is started, frame sequential illumination light made up of R light, G light and B light is outputted to the light guide 6. Furthermore, along with the starting of the light source apparatus 3, a synchronization signal synchronized with the rotation of the rotation filter 34 is outputted from the rotation filter control circuit 37 to the video processor 4.

The frame sequential illumination light made up of R light, G light and B light is outputted to an object via the light guide 6 and the illumination optical system 21.

The image of the object illuminated with the frame sequential illumination light made up of R light, G light and B light is formed by the objective optical system 22, picked up by the CCD 23 and then sequentially outputted to the video processor 4 as an image pickup signal.

The image pickup signal outputted to the video processor 4 is amplified by the amplifier 42, subjected to processing such as correlation double sampling by the process circuit 43, converted to a digital image signal by the A/D converter 44, and then inputted to the color component storage circuit 61.

Here, write timing and read timing of each color component in the color component storage circuit 61 will be described. Immediately after the starting of the video processor 4 (initial state), suppose none of the color components is stored in each memory of the R component storage circuit 61r, the G component storage circuit 61g and the B component storage circuit 61b. Hereinafter, suppose the selector 61s performs a write ("Write" shown in FIG. 5) to the color component storage circuit 61 and the calculation processing circuit 62 performs a read ("Read" shown in FIG. 5) from the color component storage circuit 61.

First, as shown in FIG. 5, immediately after the starting of the video processor 4, a color component R1 corresponding to the image of the object of R light at the first rotation (first cycle) of the rotation filter 34 is written to the memory 61r1, a color component G1 corresponding to the image of the object of G light at the first rotation (first cycle) of the rotation filter 34 is written to the memory 61g1 and a color component B1 corresponding to the image of the object of B light at the first rotation (first cycle) of the rotation filter 34 is written to the memory 61b1.

After that, as shown in FIG. 5, a color component R2 corresponding to the image of the object of R light at the second rotation (second cycle) of the rotation filter 34 is written to the memory 61r2.

As shown in FIG. 5, the color components R1 and R2 stored in the memory 61r1 and the memory 61r2 are read at the same timing as a color component G2 corresponding to the image of the object of G light at the second rotation (second cycle) of the rotation filter 34 is written to the memory 61g2.

As shown in FIG. 5, the color components G1 and G2 stored in the memories 61g1 and 61g2 are read at the same timing as a color component B2 corresponding to the image of the object of B light at the second rotation (second cycle) of the rotation filter 34 is written to the memory 61b2.

As shown in FIG. 5, the color components B1 and B2 stored in the memories 61b1 and 61b2 are read at the same timing as a color component R3 corresponding to the image of the object of R light at the third rotation (third cycle) of the rotation filter 34 is overwritten to the memory 61r1.

As shown in FIG. 5, the color components R3 and R2 stored in the memories 61r1 and 61r2 are read at the same timing as a color component G3 corresponding to the image of the object of G light at the third rotation (third cycle) of the rotation filter 34 is overwritten to the memory 61g1.

As shown in FIG. 5, the color components G3 and G2 stored in the memories 61g1 and 61g2 are read at the same timing as a color component B3 corresponding to the image of the object of B light at the third rotation (third cycle) of the rotation filter 34 is overwritten to the memory 61b1.

The above described writes and reads are repeatedly performed, and two R components; the first R component inputted at predetermined timing and the second R component inputted at timing preceding the predetermined timing by one cycle are thereby stored in the memories 61r1 and 61r2.

The above described writes and reads are repeatedly performed, and two G component; the first G component inputted at predetermined timing and the second G component inputted at timing preceding the predetermined timing by one cycle are thereby stored in the memories 61g1 and 61g2.

The above described writes and reads are repeatedly performed, and two B components; the first B component inputted at predetermined timing and the second B component inputted at timing preceding the predetermined timing by one cycle are thereby stored in the memories 61b1 and 61b2.

On the other hand, the calculation processing circuit 62 sequentially reads the first and second R components, the first and second G components, and the first and second B components at the aforementioned different timings with reference to FIG. 5 and then applies image correction processing to the information on the read color components.

Here, noise reduction processing will be described as an example of image correction processing performed by the calculation processing circuit 62. Suppose the following descriptions on the image correction processing will be given by taking mainly the processing on the first and second R components as an example.

After acquiring a difference image between the first and the second R components, the calculation processing circuit 62 applies a Fourier transform to the difference image, and thereby converts the difference image from real space data to spatial frequency data. That is, a motion component of real space data having high correlation with neighboring pixels is converted as a peak component which is intensively distributed on a specific frequency domain of spatial frequency data. On the other hand, a noise component of real space data having low correlation with neighboring pixels is converted as a component substantially uniformly distributed over each frequency domain of spatial frequency data.

After extracting each component remaining after removing the peak component as a noise component of the real space data, the calculation processing circuit 62 performs processing of subtracting each brightness value included in the noise component from the second R component. The calculation processing circuit 62 then outputs the second R component after applying the processing to the white balance circuit 45 as a color component signal.

The above described noise reduction processing is applicable not only to the R component but also to the G component and the B component likewise.

The calculation processing circuit 62 can improve S/N for each color component by performing the above described noise reduction processing as image correction processing.

Furthermore, motion interpolation processing will be described as an example of image correction processing performed by the calculation processing circuit 62.

After acquiring a difference image between the first R component and the second R component, the calculation processing circuit 62 extracts a region surrounded by a portion where the brightness value is not 0 as a region where a motion component is estimated to have been generated.

The calculation processing circuit 62 acquires a reference region of the second R component as a block based on the extracted region and then detects a region having the highest similarity to the block in the first R component. The calculation processing circuit 62 then calculates a motion vector M(dx, dy) of the block based on the coordinate position of the block and the coordinate position of the region having the highest similarity to the block.

In this case, when the brightness value at a position (x, y) of a second R component Ri is assumed to be Ri(x, y) and the brightness value at a position (x, y) of a first R component Ri+1 is assumed to be Ri+1(x, y), the relationship expressed by the following equation (1) holds between Ri(x, y), Ri+1(x, y) and motion vector M(dx, dy).

$$Ri+1(x,y)=Ri(x+dx, y+dy) \quad (1)$$

Since the above described equation (1) holds, when, for example, the aforementioned motion vector M(dx, dy) is trisected, a brightness value Rit1(x, y) at a position (x, y) of a first intermediate image Rit1 interpolated between the second R component and the first R component is expressed by the following equation (2).

$$Rit1(x,y)=Ri(x+dx \times 1/3, y+dy \times 1/3) \quad (2)$$

Furthermore, a brightness value Rit2(x, y) at a position (x, y) of a second intermediate image Rit2 interpolated between the second R component and the first R component is expressed by the following equation (3).

$$Rit2(x,y)=Ri(x+dx \times 2/3, y+dy \times 2/3) \quad (3)$$

However, when each intermediate image interpolated between the second R component and the first R component is calculated by the above described equation (2) and equation (3), there is a possibility that any one of an overlapping pixel through which the block passes a plurality of times and a gap pixel through which the block never passes may occur according to the deviation of the motion vector M(dx, dy). (The number of times the block passes therethrough can be regarded as having the same value as the number of times the motion vector M crosses, for example). The presence of the overlapping pixel and the gap pixel causes pixels having wrong brightness values to be outputted when each intermediate image is calculated.

Therefore, the calculation processing circuit 62 performs processing of assigning a brightness value of the pixel at the same position of the second R component to the brightness values of the overlapping pixel and the gap pixel in each intermediate image detected based on the number of times the block passes. This allows the calculation processing circuit 62 to avoid outputting of pixels having wrong brightness values when each intermediate image is calculated.

Here, timing at which each intermediate image is calculated will be described by taking the timing chart in FIG. 5 as an example.

The calculation processing circuit 62 reads the color components R1 and R2 at substantially the same timing as the color component R2 corresponding to the image of the object of R light at the second rotation (second cycle) of the rotation filter 34 is written to the memory 61$r$2, calculates a brightness value R1(x, y) at a position (x, y) of the color component R1, a brightness value R2(x, y) at a position (x, y) of the color component R2 and the motion vector M(dx, dy) and outputs the color component R1 to the white balance circuit 45 as a color component signal.

Furthermore, the calculation processing circuit 62 performs the calculation using the above described equation (2) at timing at which the color component G2 corresponding to the image of the object of G light at the second rotation (second cycle) of the rotation filter 34 is written to the memory 61$g$2, thereby generates a first intermediate image R1$t$1 interpolated between the color component R1 and the color component R2 and outputs the first intermediate image R1$t$1 to the white balance circuit 45 as a color component signal.

Furthermore, the calculation processing circuit 62 performs the calculation using the above described equation (3) at timing at which the color component B2 corresponding to the image of the object of B light at the second rotation (second cycle) of the rotation filter 34 is written to the memory 61$b$2, thereby generates a second intermediate image R1$t$2 interpolated between the color component R1 and the color component R2 and outputs the second intermediate image R1$t$2 to the white balance circuit 45 as a color component signal.

The calculation processing circuit 62 then reads the color components R3 and R2 at substantially the same timing as the color component R3 corresponding to the image of the object of R light at the second rotation (third cycle) of the rotation filter 34 is written to the memory 61$r$1, calculates a brightness value R2(x, y) at a position (x, y) of the color component R2, a brightness value R3(x, y) at a position (x, y) of the color component R3 and a new motion vector M(dx, dy) and outputs the color component R2 to the white balance circuit 45 as a color component signal.

That is, when the timing chart in FIG. 5 is taken as an example, the calculation processing circuit 62 generates (and outputs) two intermediate images of R1t1 and R1t2 in synchronization with the timing at which a color component other than the R component is written to the color component storage circuit 61 after the color component R1 is outputted until the color component R2 is outputted and thereby performs motion interpolation on the R component.

The above described motion interpolation processing is applicable not only to the R component but also to the G component and the B component likewise.

The calculation processing circuit 62 performs the above described motion interpolation processing as image correction processing, and can thereby improve time resolution in each color component.

As the image correction processing, the calculation processing circuit 62 of the present embodiment may perform any one of noise reduction processing and motion interpolation processing or may perform motion interpolation processing after performing noise reduction processing.

On the other hand, each color component signal outputted from the calculation processing circuit 62 is subjected to white balance processing by the white balance circuit 45, synchronized by the synchronization circuit 46, subjected to processing such as gamma correction processing by the image processing circuit 47, converted to an analog video signal by the D/A converter 48 and then outputted to the monitor 5.

As described above, the endoscope apparatus 1 of the present embodiment has a frame sequential configuration capable of time-sequentially acquiring color components having information on odd-numbered fields and information on even-numbered fields and performing image correction processing using a first color component at one timing according to the rotation cycle of the rotation filter of the light source apparatus and a second color component having the same color (wavelength band) as the first color component at timing preceding the one timing by one cycle. As a result, the endoscope apparatus 1 of the present embodiment can appropriately perform image correction processing in a frame sequential configuration.

In the frame sequential configuration, when image correction processing is performed every timing at which all color components of one frame are updated, it is not until a period combining at least a period until information corresponding to a total of 6 fields made up of information on odd-numbered fields and information on even-numbered fields of three color components of red (R), green (G) and blue (B) is acquired and a period used for calculation of the image correction processing elapses that it is possible to obtain one image after the image correction processing for the first time. That is, in the frame sequential configuration, when image correction processing is performed every timing at which all color components of one frame are updated, there are problems such as a reduction of the number of times processing is performed per unit time and/or a reduction of frame rate when a moving image is outputted.

On the other hand, unlike image correction processing that is performed every timing at which all color components of one frame are updated, the endoscope apparatus 1 of the present embodiment is configured, as described above, to start image correction processing at a point in time when both the first color component at one timing corresponding to the rotation cycle of the rotation filter of the light source apparatus and the second color component of the same color (wavelength band) as that of the first color component at timing preceding the one timing by one cycle are present. Therefore, the endoscope apparatus 1 of the present embodiment can improve the number of times image correction processing is performed per unit time while suppressing the reduction of frame rate when a moving image is outputted.

Instead of the color component storage circuit 61 only applicable to a case where the CCD 23 is a progressive scanning (non-interlace scanning) CCD, the video processor 4 of the present embodiment may also be provided with, for example, a color component storage circuit 61A shown in FIG. 6 capable of appropriately performing image correction processing when the CCD 23 is an interlace scanning CCD.

As shown in FIG. 6, the color component storage circuit 61A as the color component storage section is configured by including a selector 61s that selectively outputs a color component included in an image signal from the A/D converter 44 based on a timing signal outputted from the timing generator 49, an R component storage circuit 161r that stores an R component included in the image signal from the selector 61s, a G component storage circuit 161g that stores a G component included in the image signal from the selector 61s and a B component storage circuit 161b that stores a B component included in the image signal from the selector 61s.

The R component storage circuit 161r has memories 61r1, 61r2, 61r3 and 61r4 for storing four R components; an R component of a first odd-numbered field inputted at predetermined first timing, an R component of a second odd-numbered field inputted at timing preceding the predetermined first timing by two cycles, an R component of a first even-numbered field inputted at predetermined second timing and an R component of a second even-numbered field inputted at timing preceding the predetermined second timing by two cycles.

The G component storage circuit 161g has memories 61g1, 61g2, 61g3 and 61g4 for storing four G components; a G component of the first odd-numbered field inputted at predetermined first timing, a G component of the second odd-numbered field inputted at timing preceding the predetermined first timing by two cycles, a G component of the first even-numbered field inputted at predetermined second timing and a G component of the second even-numbered field inputted at timing preceding the predetermined second timing by two cycles.

The G component storage circuit 161g has memories 61g1, 61g2, 61g3 and 61g4 for storing four G components; a G component of the first odd-numbered field inputted at predetermined first timing, a G component of the second odd-numbered field inputted at timing preceding the predetermined first timing by two cycles, a G component of the first even-numbered field inputted at predetermined second timing and a G component of the second even-numbered field inputted at timing preceding the predetermined second timing by two cycles.

The B component storage circuit 161b has memories 61b1, 61b2, 61b3 and 61b4 for storing four B components; a B component of the first odd-numbered field inputted at predetermined first timing, a B component of the second odd-numbered field inputted at timing preceding the predetermined first timing by two cycles, a B component of the first even-numbered field inputted at predetermined second timing and a B component of the second even-numbered field inputted at timing preceding the predetermined second timing by two cycles.

Here, write timing and read timing of each color component in the color component storage circuit 61A will be described. In an initial state, suppose none of the color components is stored in each memory of the R component storage circuit 161r, the G component storage circuit 161g and the B component storage circuit 161b. Hereinafter, suppose the selector 61s performs a write ("Write" shown in FIG. 7) to the color component storage circuit 61A and the calculation processing circuit 62 performs a read ("Read" shown in FIG. 7) from the color component storage circuit 61A.

First, as shown in FIG. 7, in an initial state, a color component Ro1 of the odd-numbered field corresponding to the image of the object of R light at the first rotation (first cycle) of the rotation filter 34 is written to the memory 61r1, a color component Go1 of the odd-numbered field corresponding to the image of the object of G light at the first rotation (first cycle) of the rotation filter 34 is written to the memory 61g1 and a color component Bo1 of the odd-numbered field corresponding to the image of the object of B light at the first rotation (first cycle) of the rotation filter 34 is written to the memory 61b1.

Furthermore, as shown in FIG. 7, a color component Re1 of the even-numbered field corresponding to the image of the object of R light at the second rotation (second cycle) of the rotation filter 34 is written to the memory 61r2, a color component Ge1 of the even-numbered field corresponding to the image of the object of G light at the second rotation (second cycle) of the rotation filter 34 is written to the memory 61g2 and a color component Be1 of the even-numbered field corresponding to the image of the object of B light at the second rotation (second cycle) of the rotation filter 34 is written to the memory 61b2.

After that, as shown in FIG. 7, a color component Ro2 of the odd-numbered field corresponding to the image of the object of R light at the third rotation (third cycle) of the rotation filter 34 is written to the memory 61r3.

As shown in FIG. 7, the color components Ro1 and Ro2 stored in the memories 61r1 and 61r3 are read at the same timing as the color component Go2 of the odd-numbered field corresponding to the image of the object of G light at the third rotation (third cycle) of the rotation filter 34 is written to the memory 61g3.

As shown in FIG. 7, the color components Go1 and Go2 stored in the memories 61g1 and 61g3 are read at the same timing as the color component Bo2 of the odd-numbered field corresponding to the image of the object of B light at the third rotation (third cycle) of the rotation filter 34 is written to the memory 61b3.

As shown in FIG. 7, the color components Bo1 and Bo2 stored in the memories 61b1 and 61b3 are read at the same timing as the color component Re2 of the even-numbered field corresponding to the image of the object of R light at the fourth rotation (fourth cycle) of the rotation filter 34 is written to the memory 61r4.

By repeating writes and reads related to the above described R component of the odd-numbered field, two R components are stored in the memories 61r1 and 61r3; the R component of the first odd-numbered field inputted at predetermined first timing and the R component of the second odd-numbered field inputted at timing preceding the predetermined first timing by two cycles. Furthermore, by repeating writes and reads related to the above described R component of the even-numbered field, two R components are stored in the memories 61r2 and 61r4; the R component of the first even-numbered field inputted at predetermined second timing and the R component of the second odd-numbered field inputted at timing preceding the predetermined second timing by two cycles.

By repeating writes and reads related to the above described G component of the odd-numbered field, two G components are stored in the memories 61g1 and 61g3; the G component of the first odd-numbered field inputted at predetermined first timing and the G component of the second odd-numbered field inputted at timing preceding the predetermined first timing by two cycles. Furthermore, by repeating writes and reads related to the above described G component of the even-numbered field, two G components are stored in the memories 61g2 and 61g4; the G component of the first even-numbered field inputted at predetermined second timing and the G component of the second odd-numbered field inputted at timing preceding the predetermined second timing by two cycles.

By repeating writes and reads related to the above described B component of the odd-numbered field, two B components are stored in the memories 61b1 and 61b3; the B component of the first odd-numbered field inputted at predetermined first timing and the B component of the second odd-numbered field inputted at timing preceding the predetermined first timing by two cycles. Furthermore, by repeating writes and reads related to the above described B component of the even-numbered field, two B components are stored in the memories 61b2 and 61b4; the B component of the first even-numbered field inputted at predetermined second timing and the B component of the second odd-numbered field inputted at timing preceding the predetermined second timing by two cycles.

The endoscope 2 of the present embodiment is not limited to one having an (e.g., elongated) insertion portion that allows the light guide 6 for transmitting red, green and blue illumination light time-sequentially supplied from the light source apparatus 3 to be inserted therein, but the endoscope 2 may also be a capsule-shaped one that incorporates red, green and blue LEDs that time-sequentially emit light.

Furthermore, in the present embodiment, any one of R light, G light and B light as frame sequential light may be substituted by special light such as excitation light for generating fluorescent light from living tissue or light in an infrared region.

The present invention is not limited to the aforementioned embodiment and it goes without saying that various modifications and applications can be made without departing from the spirit and scope of the invention.

What is claimed is:

1. A medical image processing apparatus to which a plurality of color components corresponding to frame-sequentially picked-up images of an object are time-sequentially inputted while maintaining periodicity thereof, the medical image processing apparatus comprising:
   a color component storage section that can store a first color component as one color component, among the plurality of color components, which is inputted to the medical image processing apparatus at one timing and a second color component, which is the one color component inputted to the medical image processing apparatus at timing preceding the one timing by one cycle or more; and
   an image correction processing section that simultaneously reads the first color component and the second color component stored in the color component storage section and performs image correction processing, wherein:
      the image correction processing section includes a pseudo color component generation section that generates a pseudo color component of the one color component between the one timing and the timing preceding the one timing by one cycle or more, from the first color component and the second color component, and performs motion interpolation processing using the pseudo color component generated by the pseudo color component generation section, and the pseudo color component generation section includes a motion vector calculation section that calculates a motion vector between the first color component and the second color component, and generates the pseudo component using the motion vector calculated by the motion vector calculation section, the first color component, and the second color component.

2. The medical image processing apparatus according to claim 1, wherein the second color component is inputted at timing preceding the one timing by one cycle.

3. The medical image processing apparatus according to claim 1, wherein the second color component is inputted at timing preceding the one timing by two cycles.

4. A medical image pickup system comprising:
a light source section that time-sequentially outputs a plurality of illumination lights of different color components;
a color component acquiring section that can receive returned light from an object illuminated with the illumination lights and acquires color components of the object corresponding to the returned light;
a color component storage section that can store a first color component as a color component of an illumination light having one color component among the plurality of illumination lights, which is emitted from the light source section and acquired by the color component acquiring section at one timing and a second color component as the color component of the illumination light having the one color component, which has been emitted by the light source section and acquired by the color component acquiring section at timing preceding the one timing by one cycle or more; and
an image correction processing section that simultaneously reads the first color component and the second color component stored in the color component storage section and performs image correction processing, wherein:

the image correction processing section includes a pseudo color component generation section that generates a pseudo color component of the one color component between the one timing and the timing preceding the one timing by one cycle or more, from the first color component and the second color component, and performs motion interpolation processing using the pseudo color component generated by the pseudo color component generation section, and the pseudo color component generation section includes a motion vector calculation section that calculates a motion vector between the first color component and the second color component, and generates the pseudo color component using the motion vector calculated by the motion vector calculation section, the first color component, and the second color component.

5. The medical image pickup system according to claim 4, wherein the second color component is acquired at timing preceding the one timing by one cycle.

6. The medical image pickup system according to claim 4, wherein the second color component is acquired at timing preceding the one timing by two cycles.

7. The medical image pickup system according to claim 4, wherein the color component acquiring section is an image pickup device that picks up an image of the object illuminated with the illumination light and acquires a color component corresponding to the image of the object.

8. The medical image processing apparatus according to claim 1, wherein, when the first color component and the second color component are stored in the color component storage section, the image correction processing section simultaneously reads the first color component and the second color component stored in the color component storage section, and performs image correction processing.

9. The medical image pickup system according to claim 4, wherein, when the first color component and the second color component are stored in the color component storage section, the image correction processing section simultaneously reads the first color component and the second color component stored in the color component storage section, and performs image correction processing.

* * * * *